United States Patent [19]

Hanslik

[11] Patent Number: 4,541,270
[45] Date of Patent: Sep. 17, 1985

[54] APPARATUS FOR TESTING PLASTIC COMPOSITIONS

[75] Inventor: Wilhelm Hanslik, Vienna, Austria

[73] Assignee: American Maplan Corporation, McPherson, Kans.

[21] Appl. No.: 585,321

[22] Filed: Mar. 1, 1984

[51] Int. Cl.⁴ .......................................... G01N 11/08
[52] U.S. Cl. ...................................................... 73/56
[58] Field of Search ............................... 73/56, 55, 59

[56] References Cited

U.S. PATENT DOCUMENTS

| 2,674,104 | 4/1954 | Street | 73/59 X |
| 3,800,597 | 4/1974 | Paul et al. | 73/59 |
| 4,033,557 | 7/1977 | Kromer et al. | 73/59 X |

FOREIGN PATENT DOCUMENTS

| 2454600 | 5/1976 | Fed. Rep. of Germany | 73/56 |
| 1444000 | 5/1966 | France | 73/56 |
| 319633 | 1/1970 | Sweden | 73/56 |
| 188121 | 11/1966 | U.S.S.R. | 73/56 |

Primary Examiner—Stewart J. Levy
Assistant Examiner—Joseph W. Roskos
Attorney, Agent, or Firm—Karl F. Ross; Herbert Dubno

[57] ABSTRACT

An apparatus for the laboratory testing of plastic compositions as to their extrudability comprises a housing with two mutually parallel, intersecting cylindrical bores occupied by two counterrotating plasticizing screws each having two sections with threads of mutually opposite pitch separated by a gap. The gaps of the two screws are relatively offset to define a recirculation zone in which a plastic mass to be tested, fed in axially by intermeshing thread sections of these screws, is transported in one axial direction by an extension of a thread section of one screw and in the opposite axial direction by an overlapping extension of a thread section of the other screw. In the recirculation zone, in which the turns of the overlapping thread-section extensions have the same pitch, clashing is avoided by reducing the sum of the radii of these turns to less than the spacing of their axes or providing the turns with discontinuities enabling them to pass by one another. The instrument continuously records pressure and temperature at the gaps as well as the torque applied to the screws by their drive.

5 Claims, 5 Drawing Figures

APPARATUS FOR TESTING PLASTIC COMPOSITIONS

FIELD OF THE INVENTION

My present invention relates to an apparatus for the testing, e.g. in a laboratory, of plastic compositions for their extrudability.

BACKGROUND OF THE INVENTION

An apparatus for this description, which has come into commerce under the designation "Plastograph", comprises a housing with two mutually parallel and intersecting cylindrical bores accommodating respective counterrotating plasticizing screws in intermeshing relationship. These screws are designed to simulate the conditions existing in a thin-screw extruder but are to retain an introduced plastic composition in order to enable a continuous monitoring of certain parameters—especially temperature, pressure and viscosity—during mastication and plastification. Thus, whereas the actual extruder continuously ejects part of the plastic mass circulating therein, e.g. under a discharge pressure of about 300 Kg/cm$^2$, the testing apparatus referred to has no outlet. Instead, each screw is provided with two oppositely pitched thread sections which are axially separated by an intervening gap toward which the mass to be tested is being propelled from both ends, the two gaps being aligned with each other to define a region in which the mass remains more or less stationary. While this enables a measurement of the aforementioned parameters over an extended period, it does not effectively reproduce the conditions prevailing in an actual extruder.

OBJECTS OF THE INVENTION

The object of my present invention, therefore, is to provide a testing apparatus for the purpose described which more closely approximates the operating conditions of a twin-screw extruder and, in particular, enables a continuous circulation of the material being tested.

SUMMARY OF THE INVENTION

The apparatus according to my invention differs from the one described above, essentially by the fact that the two gaps of the counterrotating plasticizing screws are no longer aligned but are axially offset from each other so as to leave between them a region which can be termed a recirculation zone and in which the plastic mass, introduced through at least one inlet remote from that zone, is entrained by mutually overlapping extensions of opposite thread sections of the two screws so as to move in the vicinity of each screw toward the respective gap thereof. The applied torque is continuously monitored by first sensing means coupled with the drive means serving for the counterrotation of the two screws; pressure and temperature are continuously monitored by second and third sensing means disposed in the recirculation zone. Such sensors are, of course, well known in the art; the torquemeter, for example, may comprise a shaft coupling with a strain gauge or a wattmeter in the energizing circuit of the drive motor.

The mutually overlapping thread-section extensions of the two counterrotating screws have turns of the same pitch in the recirculation zone so that special precautions are needed to prevent them from clashing with each other. One possibility is to reduce the radii of these turns so that they no longer intermesh, in contrast to the oppositely pitched turns of the interengaging thread sections axially adjoining the ends of the recirculation zone. This means that adjacent turns of the two screws in the region of overlap should have radii whose sum is less than the spacing of the screw axes from each other. Another possibility is to provide the turns of the overlapping extensions with discontinuities giving passage to one another during their opposite rotation at identical speeds.

BRIEF DESCRIPTION OF THE DRAWING

The above and other features of may invention will now be described in detail with reference to the accompanying drawing in which.

SPECIFIC DESCRIPTION

Figure 1:
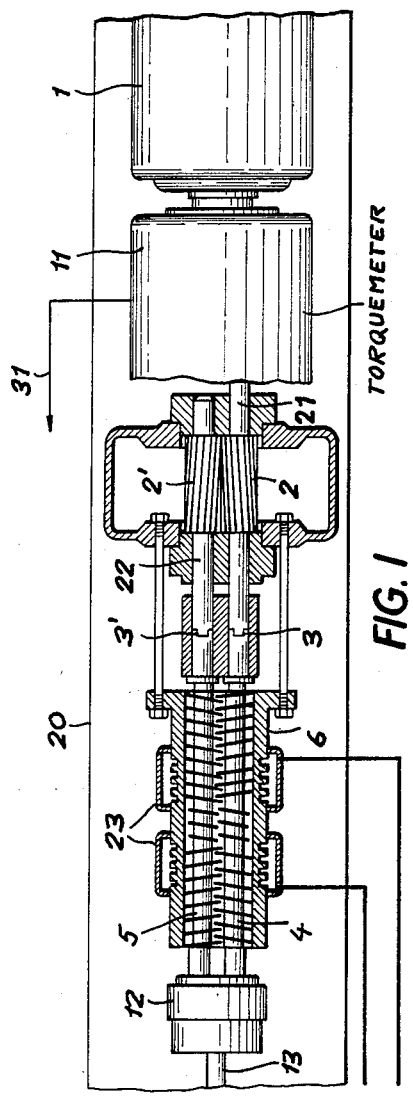
FIG. 1 is a sectional top view of an extrudability-testing apparatus embodying my invention.

The apparatus shown in FIG. 1 comprises a bed 20 supporting an electric motor 1, provided with a stepdown transmission which continuously drives a shaft 21 via a conventional torquemeter 11. Shaft 21 is keyed to a pinion 2 which meshes with a pinion 2' on a shaft 22. The two shafts 21, 22 are connected via respective clutches 3 and 3' with respective plasticizing screws 4 and 5 which are thus continuously counterrotated, with screw 4 turning counterclockwise and screw 5 turning clockwise as seen in the cross-sectional view of FIG. 5. These screws are lodged in respective bores 14, 15 of a housing 6, FIGS. 2-5, which merge into each other to form a space of figure-8 cross-section as likewise best seen in FIG. 5. The free ends of the screws are journaled in respective bearings of a mount 12 having a stem 13 to enable an extraction of the screws from their housing, together with mount 12, toward the left as viewed in FIG. 1. As further shown in this Figure, housing 6 is provided with external heaters 23 designed to keep a thermoplastic mass in its interior at a suitable temperature.

Figure 2:
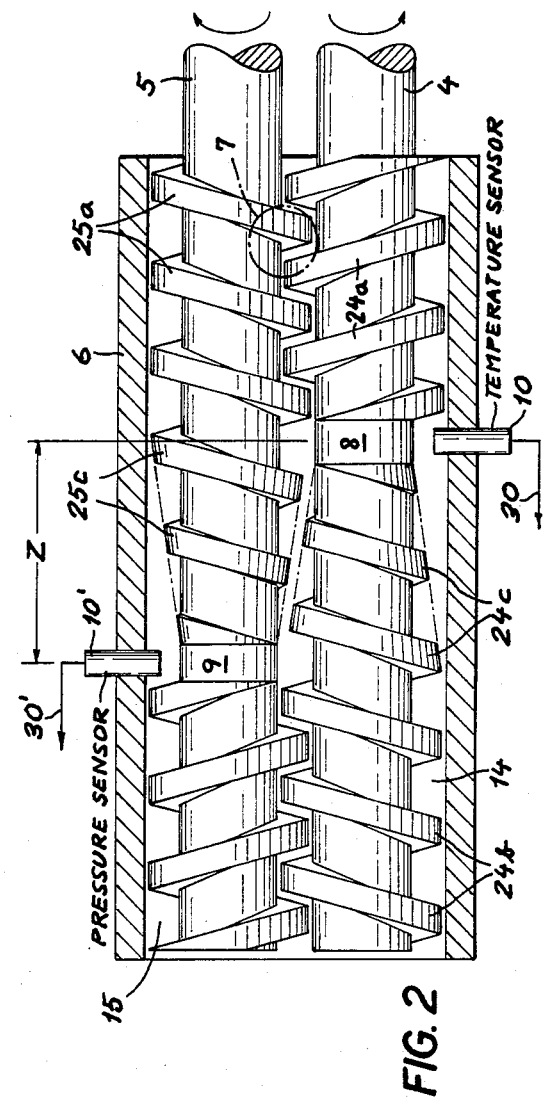
FIG. 2 is an axial sectional view of a screw assembly forming part of the apparatus of FIG. 1, drawn to a larger scale.

As illustrated in FIG. 2, screw 4 has two thread sections 24a, 24b with turns of opposite pitch respectively meshing with inversely pitched turns of thread sections 25a and 25b of screw 5. Thread sections 24a and 24b of screw 4 are axially separate from each other by a gap 8 in which the radii of their turns go to zero. A similar gap 9 axially separates the thread sections 25a and 25b of screw 5 from each other, the two gaps being axially spaced apart by a distance Z defining a recirculation zone. A temperature sensor 10 and a pressure sensor 10' in gaps 8 and 9 have output leads 30, 30' extending, together with a similar output lead 31 of the torquemeter 11 of FIG. 1, to a nonillustrated recorder which writes their readings on graph paper in the form of three continuous curves when the apparatus is in operation.

As further shown in FIG. 2, thread section 24b of screw 4 has an extension 24c with turns of progressively decreasing radius lying on an imaginary frustoconical surface. A similar extension 25c of thread section 25a of screw 5 overlaps the extension 24c within zone Z and has turns whose radii also progressively decrease along an imaginary frustoconical surface converging in a direction opposite that of the surface of extension 24c. These two imaginary surfaces are so dimensioned as to approach but not intersect each other between the two gaps 8 and 9 in order to avoid any clashes between extensions 24c and 25c.

In operation, a thermoplastic composition to be tested is introduced from above into housing 6 through an inlet port 7 proximal to thread sections 24a, 25a whose position has been diagrammatically indicated in phantom lines in FIG. 2. Port 7, straddling the two bores 14 and 15, is well spaced from the recirculation zone Z; if desired, a similar port may be provided beyond the left-hand end zone Z. The port or ports may be plugged after the introduction of the plastic material whereupon the screws are set in motion, heaters 23 are energized and the output signals of torquemeter 11 (acting as a viscosity sensor), pressure sensor 10′ and temperature sensor 10 are uninterruptedly recorded as the material is continuously transported in zone Z to the left by turns 24c and to the left by turns 25c. Thus, the behavior of the thermoplastic composition can be monitored from its powdery state to full plastification or possibly thermal decomposition.

Figure 3:
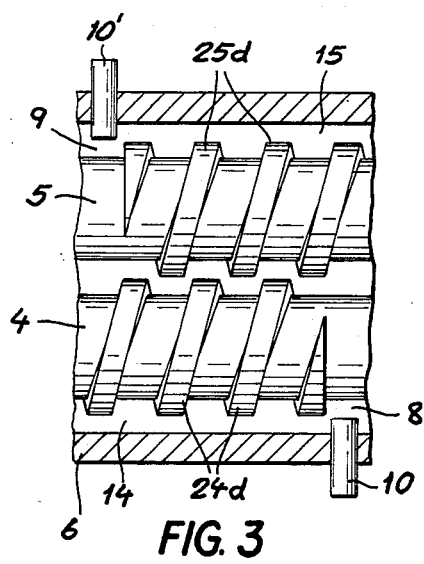
FIG. 3 is a fragmentary view of a modified screw assembly generally similar to that of FIG. 2.

As indicated in FIG. 3, turns 24d and 25d of screws 4 and 5 may be provided in the recirculation zone between gaps 8 and 9 with a uniform radius slightly less than half the spacing of the two screw axes from each other. These turns, therefore, are bounded by imaginary cylindrical surfaces of substantially smaller diameter than the bores 14 and 15.

Figure 4:
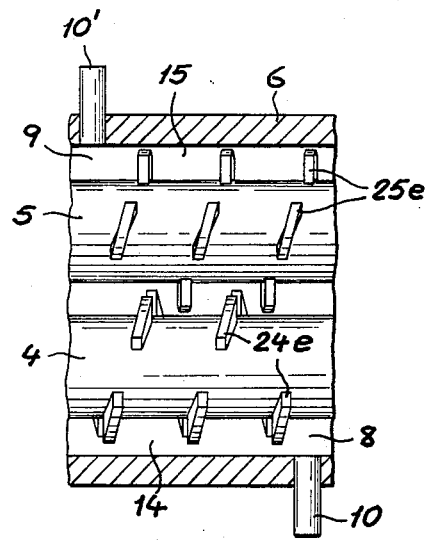
FIG. 4 is a view similar to that of FIG. 3, illustrating another modification.
Figure 5:
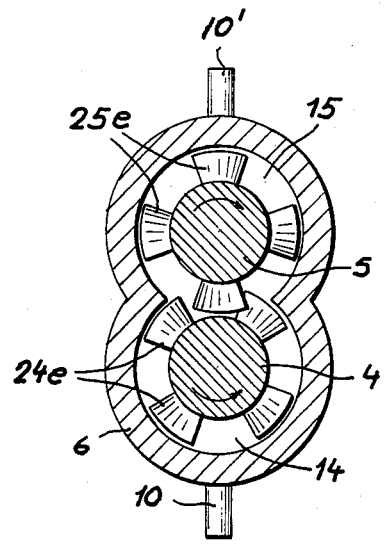
FIG. 5 is a cross-sectional view of the assembly shown in FIG. 4.

In FIGS. 4 and 5 I have shown the two counterrotating screws provided within the recirculation zone with broken turns 24e, 25e constituting, in effect, two helical rows of camming teeth spaced apart sufficiently to let each tooth 24e pass between two teeth 25e and vice versa. In this instance the radii of the turns do not decrease in the region of codirectional overlap.

In the two modifications shown in FIGS. 3–5, of course, the intermeshing thread sections of screws 4 and 5 to the right of gap 8 and to the left of gap 9, adjoining extension turns 24d, 25d and 24e, 25e, have the same configuration as sections 24a, 24b and 25a, 25b in the embodiment of FIG. 2.

In order to remove the spent mass from housing 6 after testing, the screws are extracted therefrom as discussed above. In the assembly of FIG. 3 it might be desirable to reduce the diameter of bores 14 and 15 within the recirculation zone Z in order to let the truncated turns 24d and 25d approach the inner bore walls more closely; this, however, would prevent an extraction of the screws unless the housing 6 were split into two parts along a transverse plane at the right-hand end of zone Z.

I claim:

1. An apparatus for testing the extrudability of platic compositions, comprising:
    a housing provided with two mutually parallel and intersecting cylindrical bores and with an inlet for introducing material to be tested into said bores;
    a pair of plasticizing screws in said bores provided with drive means for continuously counterrotating same, each of said screws having a first thread section proximal to said inlet and a second thread section remote from said inlet, the first and second thread sections of each screw being separated from each other by an axial gap and being formed from turns of mutually opposite pitch, the gaps of said screws being axially separated from each other by a recirculation zone axially spaced from said inlet, the turns of the first thread sections of said screws being of mutually opposite pitch and intermeshing between said inlet and said recirculation zone, the turns of the second thread sections of said screws being of mutually opposite pitch and intermeshing in a region beyond said recirculation zone, an extension of the first thread section of one screw and an extension of the second thread section of the other screw overlapping each other in said recirculation zone with turns of the same pitch shaped and dimensioned to avoid clashing with one another during counterrotation;
    first sensing means coupled with said drive means for continuously monitoring the torque applied to said screw in rotating same;
    second sensing means in said recirculation zone for continuously monitoring the pressure of a mass of plastic material transported therein by said overlapping extensions; and
    third sensing means in said recirculation zone for continuously monitoring the temperature of the transported mass.

2. An apparatus as defined in claim 1 wherein adjacent turns of said overlapping extension have radii whose sum is less than the spacing of the axes of said screws from each other.

3. An apparatus as defined in claim 2 wherein each turn of said overlapping extensions have a radius less than half the spacing of said axes.

4. An apparatus as defined in claim 1 wherein the turns of each of said overlapping sections have radii progressively decreasing toward the respective gap.

5. An apparatus as defined in claim 1 wherein the turns of each of said overlapping extensions have discontinuities giving passage to corresponding turns of the respectively opposite extension.

* * * * *